United States Patent [19]

Arrowood et al.

[11] Patent Number: 5,601,597
[45] Date of Patent: Feb. 11, 1997

[54] COMBINATION RADIAL ARTERY OCCLUDER AND WRIST SPLINT

[75] Inventors: Michael E. Arrowood; Mark Thorne, both of Raleigh; Curtis W. Thornton, Cary, all of N.C.

[73] Assignee: TAT Inc., Raleigh, N.C.

[21] Appl. No.: 557,966

[22] Filed: Nov. 13, 1995

[51] Int. Cl.$^6$ .................................................. A16F 5/00
[52] U.S. Cl. ............................... 606/203; 602/5; 128/878
[58] Field of Search ................................ 606/1, 201–204; 602/5, 20, 21, 62, 64; 128/878, 879, 898

[56] References Cited

U.S. PATENT DOCUMENTS

| 1,887,022 | 11/1932 | Hoffman et al. | 606/203 |
| 3,640,273 | 2/1972 | Ray | 128/878 |
| 4,407,277 | 10/1983 | Ellison | 606/203 |
| 4,945,925 | 8/1990 | Garcia | 128/878 |
| 5,205,812 | 4/1993 | Wasserman | 602/5 |
| 5,291,903 | 3/1994 | Reeves | 128/878 |

Primary Examiner—Michael Powell Buiz
Assistant Examiner—William Lewis
Attorney, Agent, or Firm—Rhodes, Coats & Bennett, L.L.P.

[57] ABSTRACT

A combination radial artery occluder and wrist splint used to simultaneously immobilize the wrist joint and prevent blood flow through a puncture wound or incision in the radial artery following an invasive medical procedure such as catheterization. The invention generally includes three components: a wrist splint that extends along the distal end of the patient's forearm and the back of the wrist and hand; an adjustable pressure strap attached to the splint that extends around the distal end of the forearm; and an adjustable securing strap attached to the splint that extends around the palm of the patient's hand. The pressure strap includes a pressure pad that is selectively positioned to occlude blood flow through only the radial artery while allowing blood flow through the ulnar artery. During use of the invention, the securing strap is tightened around the palm of the hand to help immobilize the wrist joint. The adjustable pressure strap is slowly tightened onto the forearm or wrist over the wound until radial artery blood flow has stopped at the wound. The invention aids hemostasis in the wound in the radial artery but allows the ulnar artery to deliver enough blood to the hand to ensure tissue viability.

12 Claims, 3 Drawing Sheets

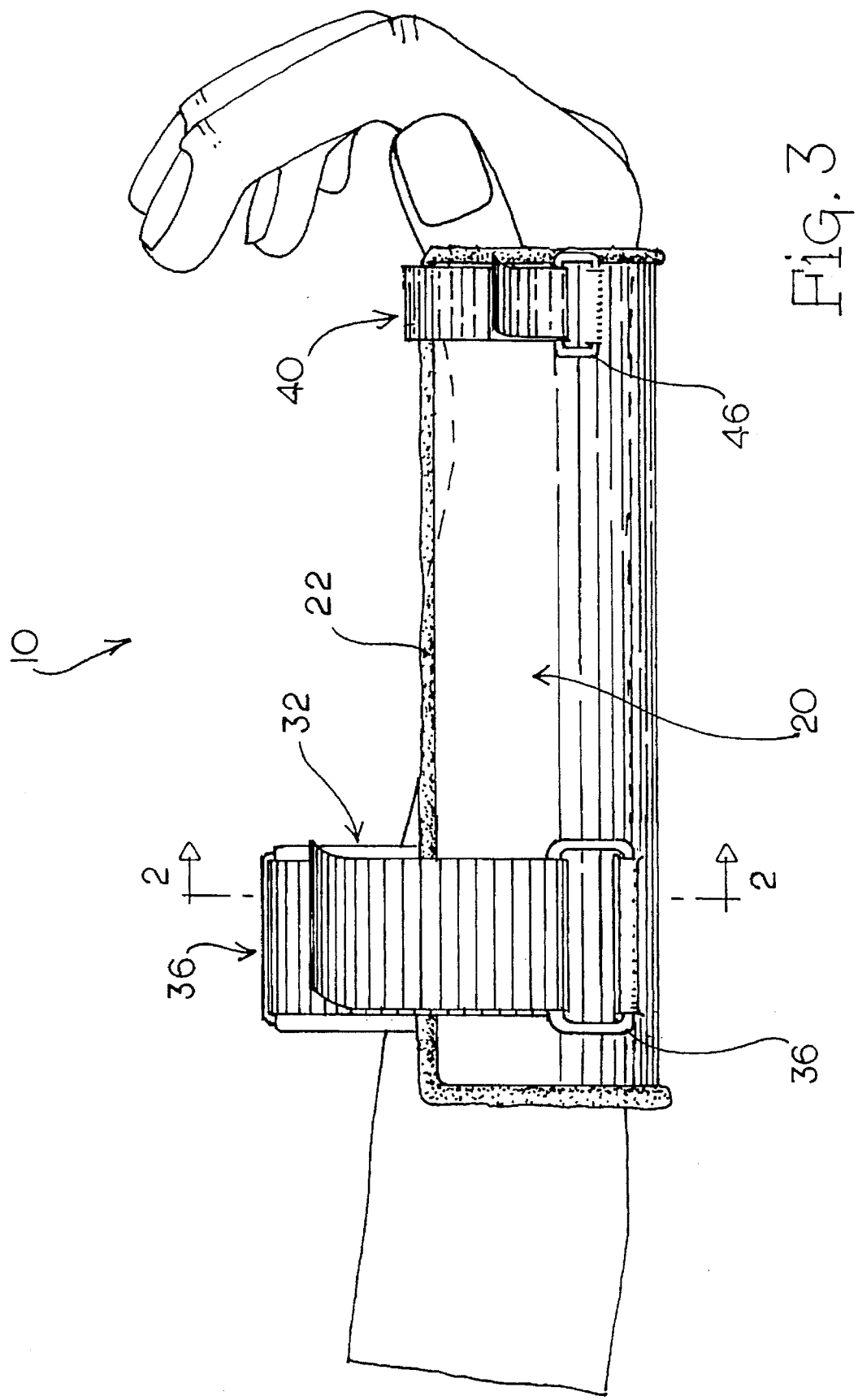

COMBINATION RADIAL ARTERY OCCLUDER AND WRIST SPLINT

FIELD OF THE INVENTION

The present invention generally relates to pressure devices for occluding blood flow and more particularly relates to a device for occluding blood flow through selected blood vessels while simultaneously immobilizing an adjacent limb joint.

BACKGROUND OF THE INVENTION

Many devices have been utilized to compress blood vessels in various parts of the body to stop the flow of blood therethrough. One of the simplest devices for stopping blood flow is a tourniquet, which is tightened around a limb to stop arterial blood flow to the distal portions of the limb and thereby minimize hemorrhaging from wounds. Several devices have improved upon the basic tourniquet, such as by applying pressure to only selected pressure points instead of around the entire circumference of the limb. Examples of such tourniquet-type devices include those disclosed in the following patents: U.S. Pat. No. 5,295,996 to Blair; U.S. Pat. No. 5,234,459 to Lee; U.S. Pat. No. 3,570,496 to Sachs; U.S. Pat. No. 2,271,927 to Saighman; and U.S. Pat. No. 1,473,041 to Henderson. Each of these devices consist of a band or strap for encircling a patient's limb, which include a pressure pad, button, or similar device to apply pressure to stop the flow of blood through the arteries of the limb.

Other tourniquet-type devices have been specifically designed to prevent bleeding through a needle puncture wound in a patient's forearm caused by, for example, blood withdrawal or an intravenous injection. U.S. Pat. No. 5,269,803 to Geary et al. discloses a hemostasis pressure pad for applying pressure to a puncture site to aid hemostasis. The device comprises an adjustable band or strap that encircles the forearm and a pressure pad that bears against the pressure site to prevent bleeding through the puncture wound. In addition, U.S. Pat. No. 3,954,109 to Patel; U.S. Pat. No. 4,005,709 to Laerdal; U.S. Pat. No. 3,586,001 to Sanderson; and U.S. Pat. No. 4,182,338 to Stanulis all disclose similar devices that include a band or strap and a pressure pad to prevent bleeding through a puncture wound in a patient's forearm.

Femoral artery cardiac catheterization procedures have led to the development of other devices designed to prevent post-catheterization wound bleeding at the femoral artery. Representative patents include the following: U.S. Pat. Nos. 5,423,852, 5,383,893, and 5,263,966 to Daneshvar; and U.S. Pat. Nos. 4,957,105 and 4,829,994 to Kurth. These devices each comprise a pelvic wrap that includes a pressure pad, balloon, or similar device for applying pressure at the wound site.

The following patents disclose additional bands or straps that are used in combination with pressure pads for purposes other than occluding the flow of blood, such as for therapeutic purposes: U.S. Pat. No. 5,372,575 to Sebastian; U.S. Pat. No. 5,312,350 to Jacobs; U.S. Pat. No. 5,135,473 to Epler et al.; U.S. Pat. No. 5,078,728 to Giarratano; U.S. Pat. No. 4,590,939 to Sakowski; U.S. Pat. No. 4,479,495 to Isaacson; U.S. Pat. No. 4,323,232 to Terpening; U.S. Pat. No. 4,308,861 to Kelly; U.S. Pat. No. 4,243,028 to Puyana; and U.S. Pat. No. 519,894 to Schutz et al.

One problem that often arises following medical procedures involving an arterial puncture is delay in hemostasis caused by movement of the wounded tissue, such as wrist movement after a radial artery cardiac catheterization procedure. Tissue stretching and contraction caused by movement of a limb joint can prevent clotting and inadvertently reopen wounds. While there are many references that disclose the broad concept of using a strap with a pressure pad to stop the flow of blood through an arterial puncture wound, none of these devices immobilize limb joints adjacent the wounded tissue. Therefore, a need exists for a device that immobilizes a limb joint while simultaneously occluding blood flow.

OBJECTS AND SUMMARY OF THE INVENTION

In view of the above, an object of the present invention is to provide a device that stops the flow of blood from wounded tissue while simultaneously immobilizing a joint adjacent the wounded tissue, thereby aiding hemostasis.

A more particular object of the present invention is to provide an arterial occluding device that stops the flow of blood from a puncture wound or incision following a medical procedure such as catheterization while at the same time immobilizing a limb joint adjacent to the puncture wound, thereby aiding hemostasis.

An even more particular object of the present invention is to provide an arterial occluding device that stops the flow of blood from a puncture wound or incision following a radial artery catheterization procedure while at the same time splinting the wrist joint, thereby aiding hemostasis.

It is yet another object of the present invention to provide a pressure-applying arterial occluding device that stops the flow of blood in only the radial artery following a radial artery catheterization procedure, permitting unencumbered blood flow to the hand through the ulnar artery, while at the same time splinting the wrist joint.

The present invention achieves these and other objects by providing a combination radial artery occluder and wrist splint to prevent blood flow through a puncture wound or incision following catheterization or similar invasive medical procedure. The device of the invention generally includes three main components: a wrist splint that extends along the distal end of the patient's forearm and the back of the wrist and hand; an adjustable pressure strap attached to the splint that extends around the distal end of the forearm; and an adjustable securing strap also attached to the splint that extends around the palm of the patient's hand. The wrist splint is preferably generally trough-shaped so as to cradle the forearm, wrist, and hand around at least approximately half the circumference thereof. Also, the wrist splint preferably includes padding on its inner, concave surface to cushion the forearm. The pressure strap includes a pressure pad that is selectively positioned over the wound in the forearm or wrist to occlude blood flow through only the radial artery while allowing blood flow to the hand through the ulnar artery. During use of the invention, the adjustable pressure strap is slowly tightened over the wound until radial artery blood flow has stopped at the wound. This aids hemostasis in the wound in the radial artery but allows the ulnar artery to deliver enough blood to the hand to ensure tissue viability. In addition, the securing strap is tightened around the palm of the hand to help immobilize the wrist joint.

Other aspects and advantages of the present invention will become apparent and obvious from a study of the following description and the accompanying drawings, which are merely illustrative of such invention.

BRIEF DESCRIPTION OF THE DRAWINGS

FIG. 3 is a side view of the device of the invention being worn by patient.

DETAILED DESCRIPTION OF THE INVENTION

Figure 1:
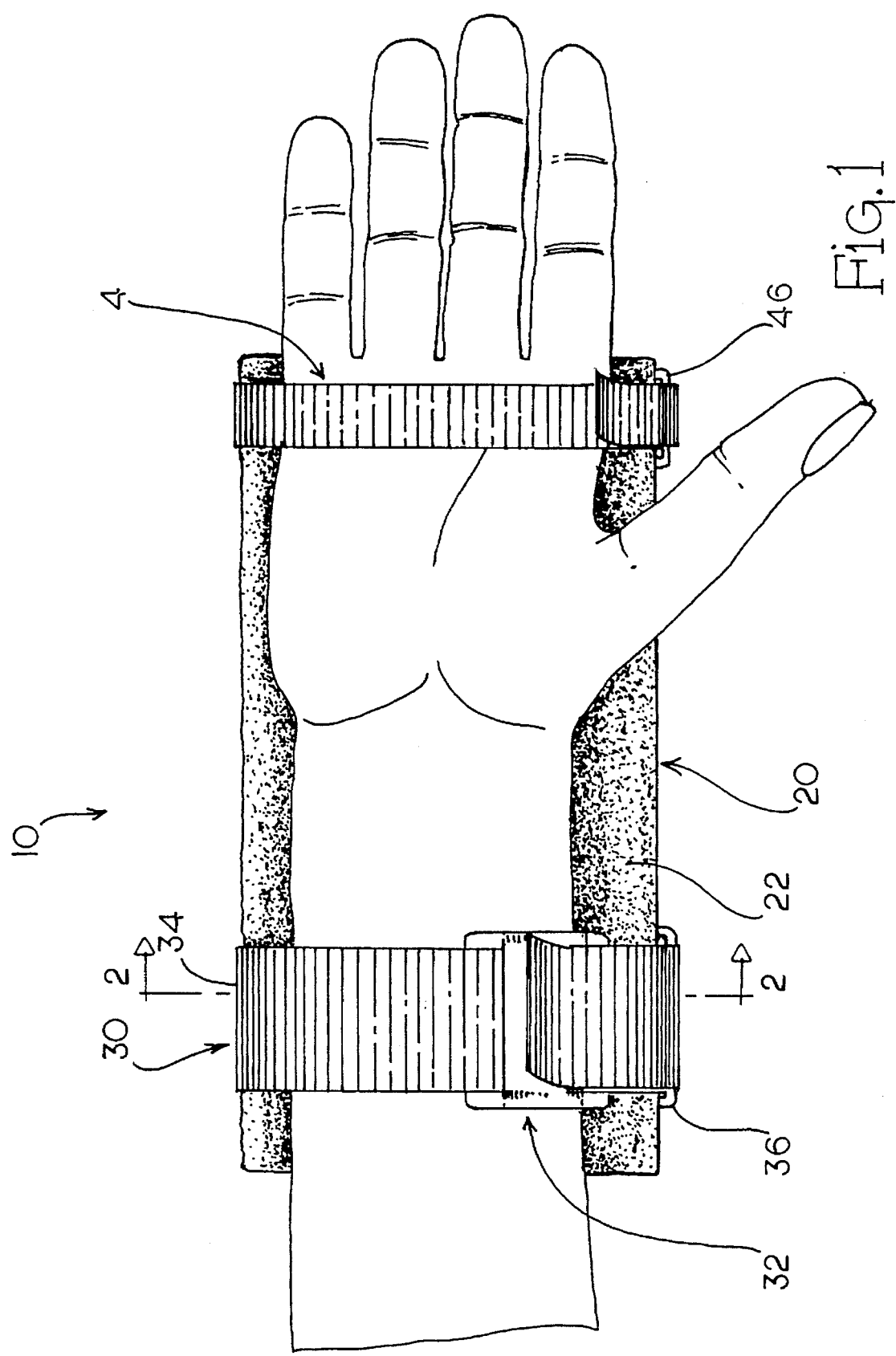
FIG. 1 is a top view of the device of the invention simultaneously occluding blood flow through the radial artery while immobilizing the wrist.

The present invention is described more fully hereinafter by referring to the drawings, in which a preferred embodiment is depicted. However, the present invention can take on many different embodiments and is not intended to be limited to the embodiments described herein.

Referring now to the drawings, a combination radial artery occluder and wrist splint, generally designated 10, is shown constructed according to the present invention. The artery occluder/splint 10 is used to stop the flow of blood from a wound resulting from a radial artery catheterization procedure while at the same time immobilizing the wrist joint, thereby aiding hemostasis. In the preferred embodiment, the artery occluder/splint 10 applies localized pressure to only the radial artery following a radial artery catheterization procedure, thereby permitting unencumbered blood flow through the ulnar artery to ensure viability of tissues in the hand. The artery occluder/splint 10 of the invention could likewise be used to aid hemostasis in any selected blood vessel of a limb following any medical procedure involving puncturing or making an incision in an artery or vein.

As shown in the drawings, the artery occluder/splint 10 generally includes three main components: a wrist splint 20 that extends along the distal end of the patient's forearm and the back of the wrist and hand; an adjustable pressure strap 30 attached to the splint 20 and extending around the distal end of the forearm; and an adjustable securing strap 40 attached to the opposite end of the splint 20 and extending around the palm of the hand. As described herein, the artery occluder/splint 10 is particularly designed to be worn on the wrist subsequent to a radial artery cardiac catheterization procedure. However, it is conceivable that the artery occluder/splint 10 could be adapted to be worn on the elbow joint or even one of the leg joints to accomplish the objectives of inducing hemostasis in an arterial wound while simultaneously immobilizing an adjacent limb joint. It is just as conceivable that the artery occluder/splint 10 of the invention could be used on the arms and/or legs of animals in addition to its contemplated use with humans.

In the disclosed embodiment, the splint 20 is generally trough-shaped, being formed by bisecting a hollow cylinder along a longitudinal plane thereof. The splint 20 is preferably formed so as to cradle the forearm, wrist, and hand around at least approximately half the circumference thereof. Alternately, the splint could encompass less of the arm, wrist and hand than shown, although at the expense of comfort and efficacy in immobilizing the joint. The splint 20 may be formed from any relatively rigid material such as PVC. To help cushion the limb held within, the splint 20 preferably includes padding 22 on its inner, concave surface. It is envisioned that the padding 22 could be molded to conform to the contours of the forearm, wrist, and hand for an even more comfortable and secure fit.

The adjustable pressure strap 30 is attached proximate one end of the splint 20 so as to overlie the inside surface of the forearm. The pressure strap 30 includes a pressure pad 32 that may be selectively positioned to occlude blood flow through only one artery or vein. The pressure pad 32 preferably is formed from a relatively hard material, such as hard rubber or plastic, and preferably has a generally rounded shape to avoid pinching or cutting the skin. The pressure pad 32 may be fixedly attached to the pressure strap 30 or it may be moveable along the pressure strap 30. Preferably, the pressure pad 32 is moveably attached to the pressure strap 30 by, for example, having one or more slots through which the pressure strap 30 extends. During use of the artery occluder/splint 10, a conventional absorbent material such as gauze would typically be placed between the pressure pad 32 and the arterial wound.

Figure 2:
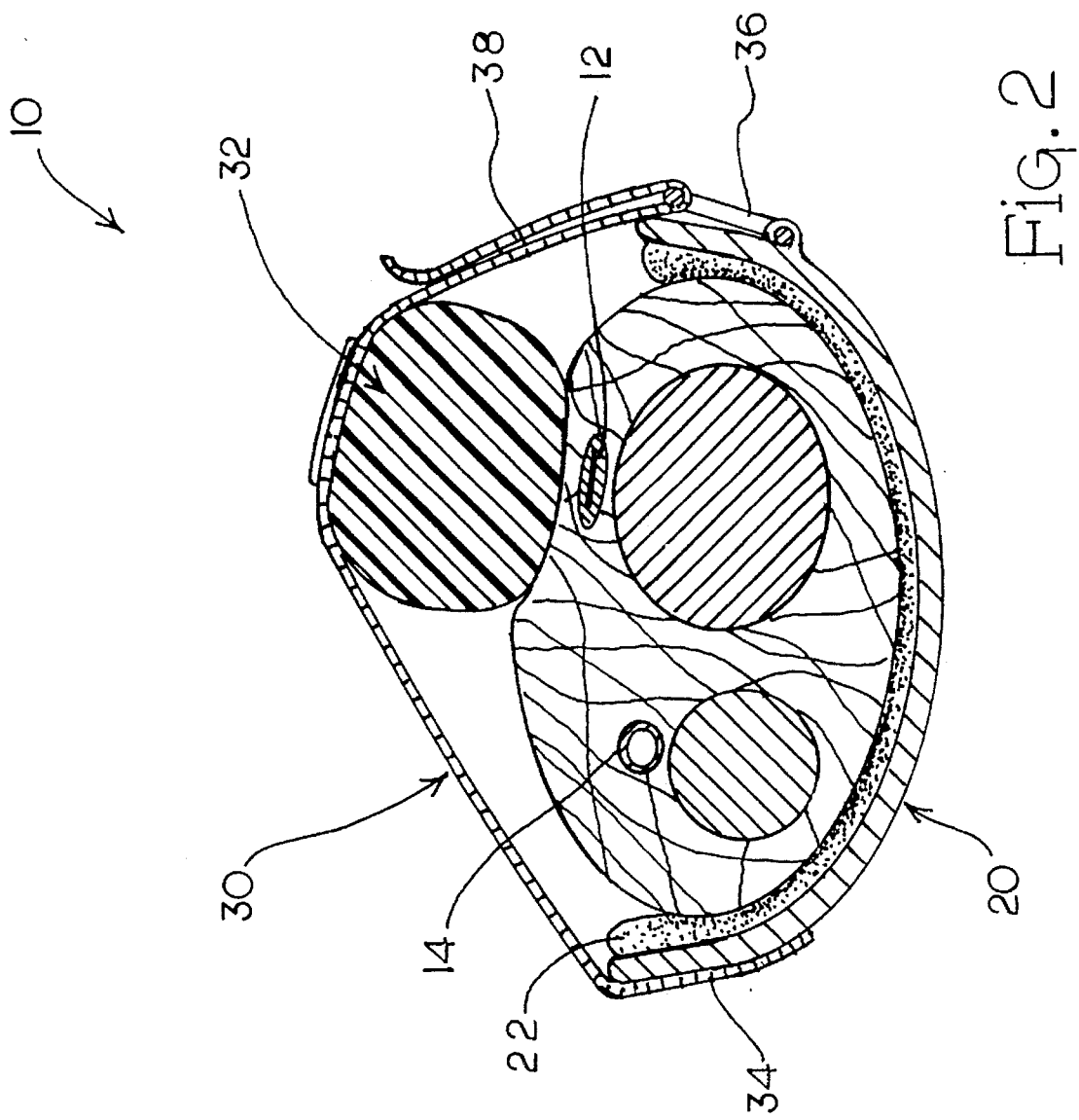
FIG. 2 is a cross-sectional view of the patient's forearm and the device of the invention, wherein the device of the invention is occluding the radial artery but permitting blood flow through the ulnar artery.

After a radial artery cardiac catheterization procedure, wherein a catheter is inserted through a puncture wound or incision in the radial artery 12, only the radial artery 12 is compressed by the pad 32, as shown in FIG. 2, while the ulnar artery 14 is allowed to remain open. This aids hemostasis in the wound in the radial artery 12 after the catheter is removed but allows the ulnar artery 14 to deliver enough blood to the hand to ensure tissue viability. Since the ulnar artery 14 continues to supply blood to the hand, the device 10 can be comfortably worn for several hours without complications caused by the restriction of blood flow through the radial artery 12.

The adjustable pressure strap 30 may be formed of any conventional strapping material that can withstand common medical sterilization procedures. Preferably, the strap 30 is attached at one end 34 to one side of the splint 20 and at the other end to a D-loop 36 attached to the other side of the splint 20. The pressure strap 30 may be looped through the D-loop 36 and folded back upon itself. The end of the pressure strap 30 can be secured by a hook and loop fastener 38, such as VELCRO. It should be understood, however, that other methods of securing the pressure strap 30 around the splint 20 and forearm could be used, such as looping a continuous strap completely around the splint. Likewise, fasteners other than the D-loop 36 and the hook and loop fastener 38 depicted herein could be used to hold the pressure strap 30 in place. For example, a buckle could be used to achieve the same objectives.

The adjustable securing strap 40 is attached proximate the opposite end of the splint 20 from the pressure strap 30 and is tightened around the palm of the hand until the wrist joint is immobilized. The securing strap 40 may also be formed of any conventional strapping material that can withstand common medical sterilization procedures. Like the pressure strap 30, the securing strap 40 is preferably attached at one end 44 to one side of the splint 20. The other end loops through a D-loop 46 attached to the splint 20. The adjustable securing strap 40 preferably includes a hook and loop fastener 48 such as VELCRO to fasten the securing strap 40 around the hand, although other conventional adjustable fasteners could be used instead.

Now turning to the preferred use of the combination radial artery occluder and wrist splint 10, the artery occluder/splint 10 is particularly designed to occlude the flow of blood through the radial artery 12 at the level of the distal aspect of the forearm subsequent to a radial artery cardiac catheterization procedure. However, in its present form, the artery occluder/splint 10 could also be used to prevent bleeding from a needle puncture wound in a patient's forearm caused by, for example, blood withdrawal or an intravenous injection. The artery occluder/splint 10 is applied to the patient as soon as feasible after the catheter or needle is removed and is left in place until hemostasis has been achieved at the arterial entry site. In a typical situation, with a patient of normal blood clotting abilities, the device 10 may be applied for up to approximately two hours.

More specifically, the steps involved in using the device 10 of the invention include the following:

1. The artery occluder/splint 10 is sterilized according to accepted medical protocols.
2. The pressure strap 30 and the securing strap 40 are both opened.
3. The affected forearm, wrist, and hand are positioned in the splint 20.
4. The pressure pad 32 is positioned over the wound in the radial artery.
5. The securing strap 40 is tightened to immobilize the patient's wrist joint in the splint 20.
6. The pressure strap 30 is slowly tightened until radial artery blood flow has stopped at the site of the wound.
7. Hemostasis is periodically checked by slowly lifting the pressure pad 32. If bleeding persists, the pressure strap 30 is re-tightened and the artery occluder/splint 10 is left in place. If bleeding has stopped, the artery occluder/splint 10 is removed.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A radial artery occluder for occluding blood flow through the radial artery following a catheterization procedure comprising:
    a) a wrist splint extending along the distal end of the patient's forearm and the back of the patient's hand, said splint having first and second ends;
    b) an adjustable pressure strap attached to a first end of said wrist splint and which extends around the distal end of the patient's forearm;
    c) a pressure-applying pad disposed along said pressure strap for localizing pressure on the radial artery of the patient to stop the flow of blood through the radial artery while allowing blood flow in the ulnar artery to continue; and
    d) an adjustable securing strap attached to a second end of the splint and which extends around the palm of the patient's hand to immobilize the patient's wrist.

2. The radial artery occluder of claim 1 wherein said splint comprises a generally c-shaped channel member.

3. The radial artery occluder of claim 2 further including padding on the inner surface of said c-shaped channel member.

4. The radial artery occluder of claim 3 wherein said pressure-applying pad is slideably mounted on said pressure strap.

5. The radial artery occluder of claim 1 wherein said pressure-applying pad is slideably mounted on said pressure strap.

6. A device for immobilizing a joint and occluding the flow of blood through a blood vessel comprising:
    a) a rigid member extending across a designated joint of a patient's body;
    b) first and second straps attached to opposite ends of said rigid member and which extend around a portion of the patient's body to secure the rigid member to the patient's body so as to immobilize the designated joint;
    c) a pressure-applying device disposed along one of said first and second straps for stopping blood flow through one or more blood vessels.

7. The device of claim 6 wherein said rigid member comprises a generally c-shaped channel member.

8. The device of claim 7 further including padding on the inner surface of said c-shaped channel member.

9. The device of claim 8 wherein said pressure-applying pad is slideably mounted on one of said first and second straps.

10. The device of claim 6 wherein said pressure applying-pad is slideably mounted on one of said first and second straps.

11. A method for occluding blood flow in the radial artery following a catheterization procedure comprising:
    a) applying a wrist splint to the patient which extends from the distal end of the patient's forearm, across the patient's wrist, to the back of the patient's hand;
    b) positioning a pressure-applying pad over the radial artery; and
    c) securing the wrist splint in place using one or more straps attached to the wrist splint so as to immobilize the patient's wrist, wherein at least one of said straps extends over the pressure-applying pad so as to apply pressure when said strap is tightened.

12. A method for occluding blood flow through a blood vessel adjacent a body joint comprising:
    a) applying a splint to the patient's body joint;
    b) positioning a pressure-applying pad over the blood vessel; and
    c) securing splint in place by extending one or more straps around a portion of the patient's body so as to immobilize the joint, wherein one of said straps extends over said pressure-applying pad so as to apply pressure when said strap is tightened.

* * * * *